US010988283B2

(12) United States Patent
Lee (10) Patent No.: US 10,988,283 B2
(45) Date of Patent: Apr. 27, 2021

(54) CASE FOR COIN TISSUE

(71) Applicant: CLEANZONE CO., LTD., Pocheon-si (KR)

(72) Inventor: Wan Gu Lee, Seoul (KR)

(73) Assignee: Cleanzone Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/552,977

(22) Filed: Aug. 27, 2019

(65) Prior Publication Data
US 2020/0299028 A1      Sep. 24, 2020

(30) Foreign Application Priority Data

Mar. 22, 2019   (KR) .................. 10-2019-0032777

(51) Int. Cl.
*A47K 10/42*    (2006.01)
*B65D 21/08*    (2006.01)
(Continued)

(52) U.S. Cl.
CPC .......... *B65D 21/086* (2013.01); *A47K 10/426* (2013.01); *A61K 8/0208* (2013.01); *A61Q 19/10* (2013.01)

(58) Field of Classification Search
CPC ...... A47K 10/32; A47K 10/42; A47K 10/421; A47K 10/426; A47K 2010/3233;
(Continued)

(56) References Cited

U.S. PATENT DOCUMENTS 2,367,019 A * 1/1945 Haag ................. B65D 83/0445
                                                  206/0.83
4,898,195 A * 2/1990 Sussman ............. A45D 33/006
                                                  206/38
(Continued)

FOREIGN PATENT DOCUMENTS

CN      2012-34949 Y    5/2009
JP      S39-6062 Y      3/1964
(Continued)

OTHER PUBLICATIONS

Office Action of Japanese Patent Application No. 2019-151912—6 pages (dated Sep. 8, 2020).

*Primary Examiner* — Bryon P Gehman
(74) *Attorney, Agent, or Firm* — Knobbe Martens Olson & Bear LLP (57) ABSTRACT

A case for coin tissue is disclosed. In one aspect, the case includes a drawer housing including an insertion space and a push-in and pull-out portion communicating with the insertion space. The case also includes a drawer configured to be pushed into or pulled out of the insertion space in a slidable manner through the push-in and pull-out portion. The drawer includes an upper opening portion. A plurality of coin tissues are placed in one or more rows in the drawer. The case further includes a pull-out distance limiting part provided between an inner surface of the drawer housing and an outer surface of the drawer, and configured to limit a pull-out distance of the drawer to a first distance. According to at least some embodiments, the case for coin tissue can sanitarily preserve a coin tissue, and is portable, and convenient.

1 Claim, 5 Drawing Sheets

(51) Int. Cl.
*A61K 8/02* (2006.01)
*A61Q 19/10* (2006.01)

(58) Field of Classification Search
CPC .... A47K 2010/3273; A47K 2010/3286; A61K 8/02; A61K 8/0208; A61Q 19/10; B65D 21/08; B65D 21/086; B65D 83/04; B65D 83/0466; B65D 83/08
USPC ................................ 206/81–0.84, 0.81–0.84
See application file for complete search history.

(56) References Cited

U.S. PATENT DOCUMENTS

| | | | |
|---|---|---|---|
| 9,186,024 B2 * | 11/2015 | Lee | ........................ A47K 10/426 |
| 10,537,212 B1 * | 1/2020 | Lee | ........................ A47K 10/421 |

FOREIGN PATENT DOCUMENTS

| | | | | |
|---|---|---|---|---|
| JP | 2003-192055 A | | 7/2003 | |
| JP | 3110587 U | | 5/2005 | |
| KR | 10-2008-0021850 A | | 3/2008 | |
| KR | 20090008919 A | * | 1/2009 | ............. A47K 10/42 |
| KR | 101247256 B1 | * | 3/2013 | ............. A47K 10/42 |
| WO | WO-2007066865 A1 | * | 6/2007 | ............. A47K 10/32 |

\* cited by examiner

CASE FOR COIN TISSUE

CROSS-REFERENCE TO RELATED APPLICATION

This application claims the benefit of Korean Patent Application No. 10-2019-0032777, filed on Mar. 22, 2019, in the Korean Intellectual Property Office, the disclosure of which is incorporated herein in its entirety by reference.

BACKGROUND

1. Field

One or more embodiments relate to a coin tissue.

2. Description of Related Art

Generally, a coin tissue, which is compressed into a coin shape and is in a dehydrated state, swells up like general wet tissue when water is poured and used in restaurants and the like.

Particularly, being compressed into a hydrated state, the coin tissue has no risk of germ propagation and does not require use of preservatives such as an antifungal agent or an antioxidant.

In the related art, a coin tissue is provided in a large amount sealed with a plastic bag or zipper bag. Therefore, a user takes out the coin tissue one by one from a plastic bag or zipper bag to use the coin tissue.

However, in the case the user takes out the coin tissue from the plastic bag or zipper bag each time of use, the user happens to touch coin tissues around the coin tissue that is taken out, and thus, the coin tissues kept in the plastic bag or zipper bag are also polluted by the user's hand. Eventually, as the user touches the coin tissue every time of use, the coin tissues are not sanitarily maintained.

In addition, as use of the coin tissue in the related art requires water provided in an extra container, the use is inconvenient.

SUMMARY

One or more embodiments include a case for coin tissue that is capable of sanitarily preserving a coin tissue, the case being portable and convenient.

One or more embodiments include a case for coin tissue which may contain water.

Additional aspects will be set forth in part in the description which follows and, in part, will be apparent from the description, or may be learned by practice of the presented embodiments of the disclosure.

According to one or more embodiments, a case for coin tissue includes: a drawer housing including an insertion space and a push-in and pull-out portion communicated with the insertion space; a drawer configured to be pushed into or pulled out of the insertion space in a slidable manner through the push-in and pull-out portion, and includes an upper opening portion, the drawer in which a plurality of coin tissues are placed in one or more rows; and a pull-out distance limiting part provided between an inner surface of the drawer housing and an outer surface of the drawer, limiting a pull-out distance of the drawer to a first distance.

The pull-out distance limiting part may include: a locking groove provided at one of the inner surface of the drawer housing and the outer surface of the drawer; and a locking protrusion provided at another one of the inner surface of the drawer housing and the outer surface of the drawing and being locked at the locking groove.

The drawer may include: a drawer body including the upper opening portion, the drawer body in which the coin tissue is placed; and a tissue pull-out guide groove formed at a side surface of the drawer body in a lower height than a height of the side surface of the drawer body, the tissue pull-out guide groove that guides the coin tissue to be pulled out.

The push-in and pull-out portion of the drawer housing may be formed by opening in a front surface of the drawer housing and have a determined size such that the coin tissue is smoothly pulled in and out while the drawer is being pulled in and out. The drawer may further include a cover that is provided at a front surface of the drawer body and closes the push-in and pull-out portion when the drawer body is pushed into the drawer housing.

The case for coin tissue may further include a wet tissue production part provided at the outer surface of the drawer housing and containing water, the wet tissue production part that accommodates the coin tissue such that the coin tissue pulled out of the drawer is soaked by the water in the wet tissue production part.

The one or more rows may include a first row and a second row, the drawer may include a first row rest part that places some of the plurality of coin tissues in the first row; the second row rest part that places others of the plurality of coin tissues in the second row; and an intermediate partition that divides the first row rest part and the second row rest part.

The wet tissue production part may be provided at an outer surface of the drawer housing in a recessed manner, and one of the first row rest part and the second row rest part may be provided in a relatively short length not to interfere with the wet tissue production part provided in the recessed manner to provide a space into which the wet tissue production part is to be recessed.

The case for coin tissue according to an embodiment of the present disclosure may further include a tilt prevention part to prevent the drawer from inclining against the drawer housing while the drawer is being pulled out.

The tilt prevention part may include: a guide rail which protrudes from the inner wall of the drawer housing and is provided long along a direction in which the drawer is pulled in and out; and a rail contact surface that constitutes an upper end of a side surface of the drawer body and slidably contacts with a bottom surface of the guide rail.

The first distance may be a thickness of the coin tissue.

A rest surface, on which the plurality of coin tissues are placed, may include a smooth surface so that the plurality of coin tissues may be moved to the front of the case when the case for coin tissue is inclined such that the front of the case faces downward.

BRIEF DESCRIPTION OF THE DRAWINGS

The above and other aspects, features, and advantages of certain embodiments of the disclosure will be more apparent from the following description taken in conjunction with the accompanying drawings.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Figure 1:
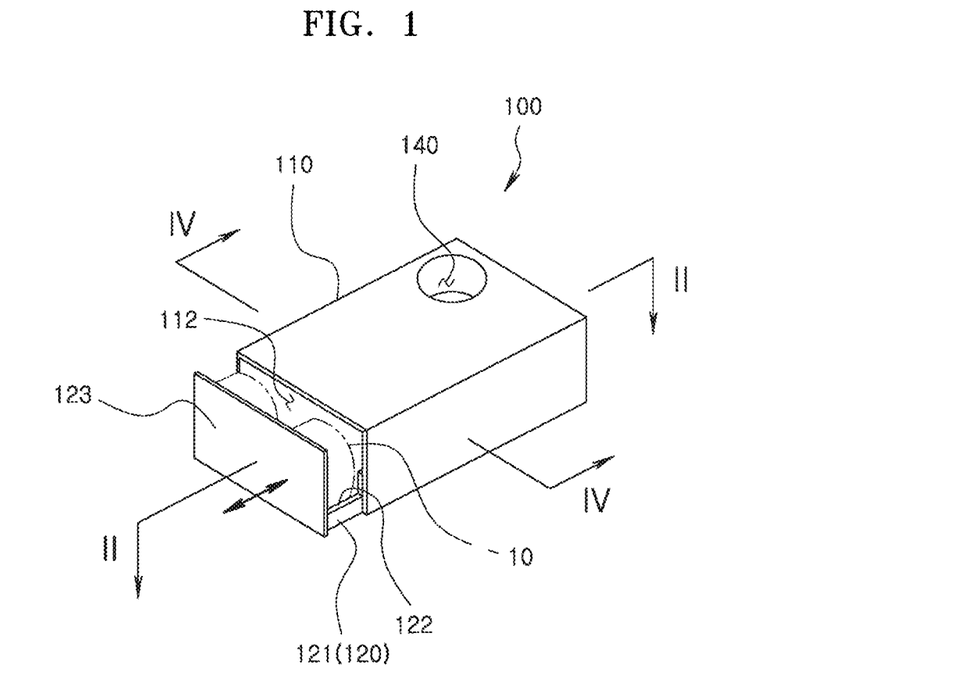
FIG. 1 is a schematic diagram of a case for coin tissue according to an embodiment of the present disclosure.
Figure 2:
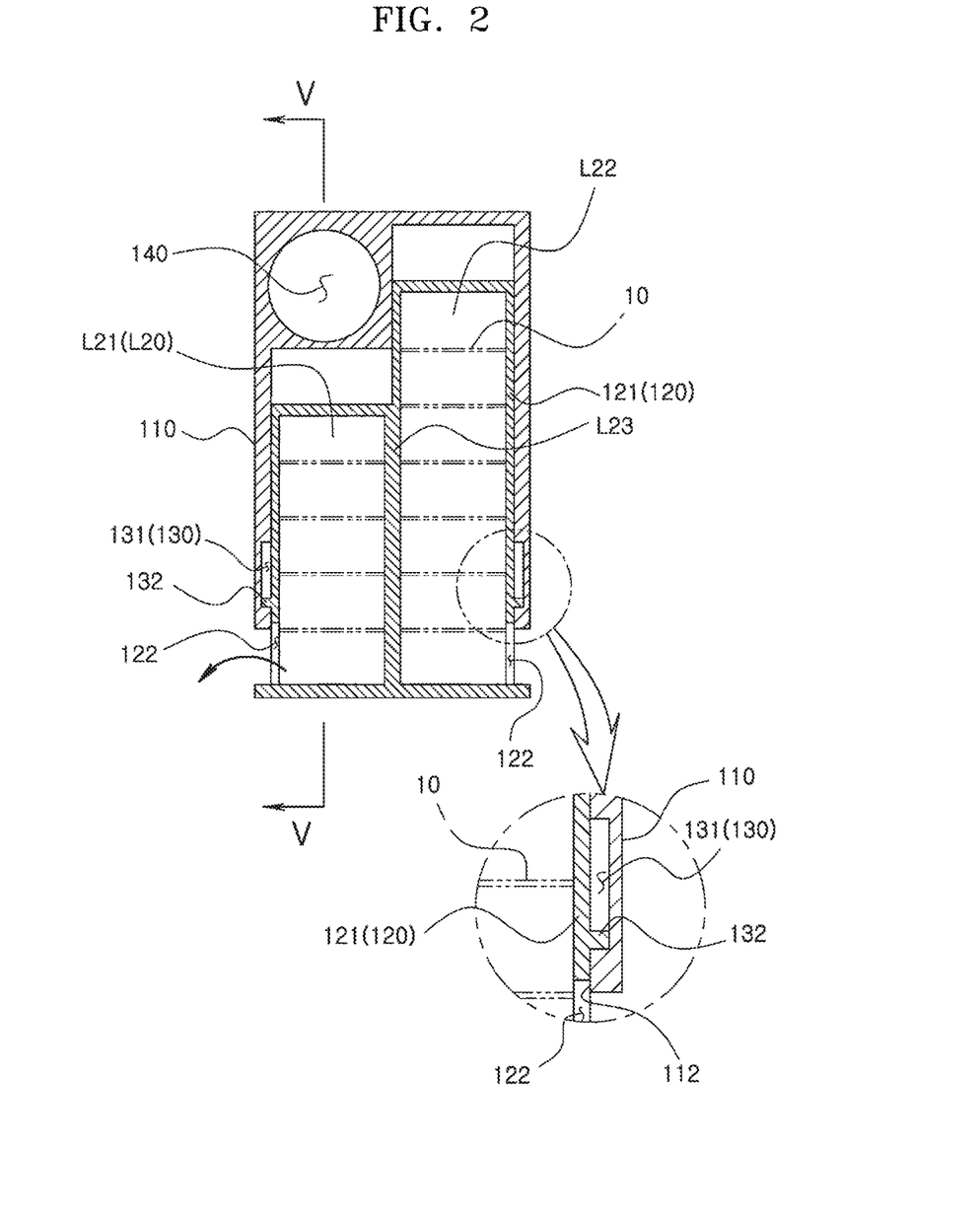
FIG. 2 is a cross-section of the case for coin tissue shown in FIG. 1, taken along line II-II.
Figure 3:
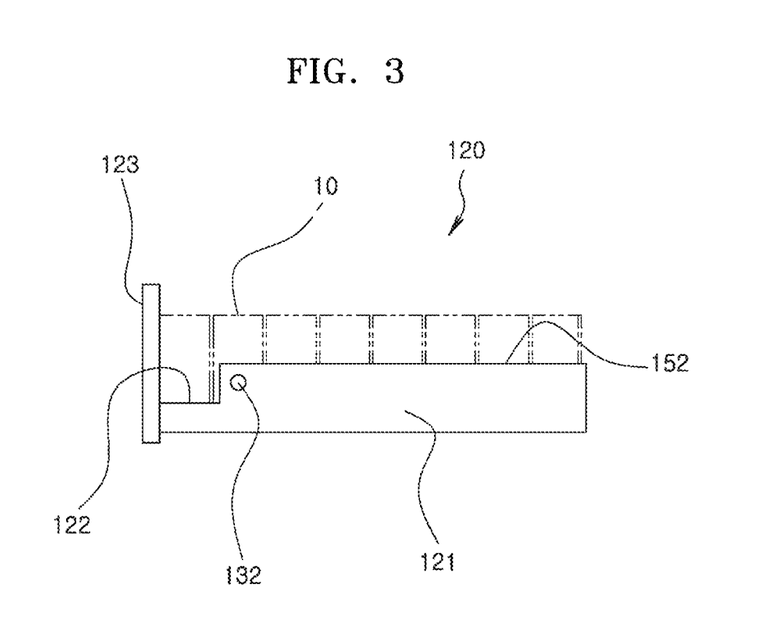
FIG. 3 is a schematic side view of a drawer in the case for coin shape tissue of FIG. 1.

FIG. 1 is a schematic diagram of a case for a coin tissue according to an embodiment of the present disclosure, FIG. 2 is a cross-section of the case for the coin tissue shown in FIG. 1, taken along line II-II, and FIG. 3 is a schematic side view of a drawer in the case for the coin tissue of FIG. 1.

Figure 4:
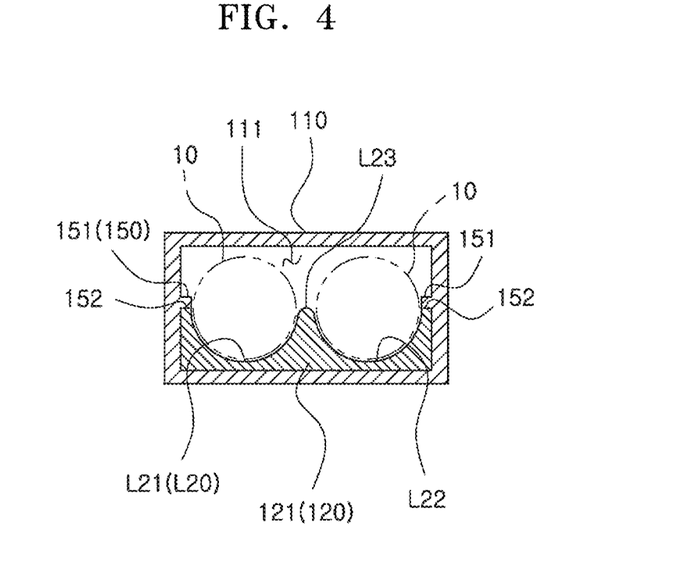
FIG. 4 is a cross-section of the case for coin shape tissue of FIG. 1, taken along line IV-IV.
Figure 5:
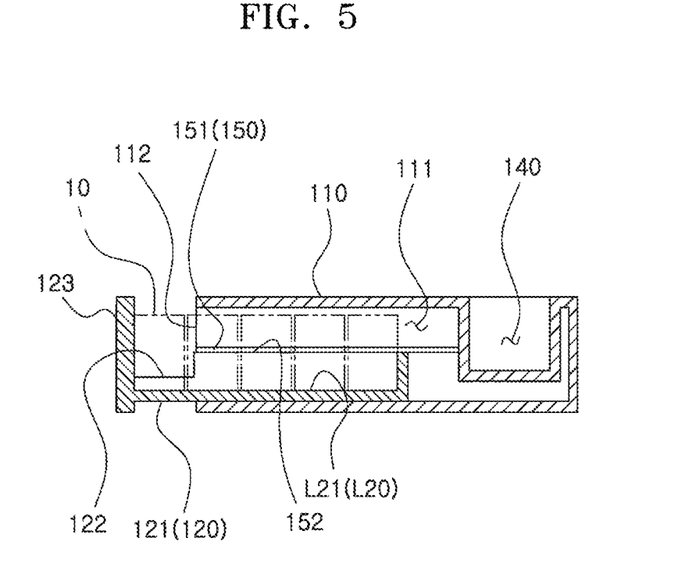
FIG. 5 is a cross-section of the case for coin tissue of FIG. 1, taken along line V-V.

FIG. 4 is a cross-section of the case for the coin tissue of FIG. 1, taken along line IV-IV, and FIG. 5 is a cross-section of the case for the coin tissue of FIG. 1, taken along line V-V.

A case 100 for coin tissue according to an embodiment of the present disclosure includes a drawer housing 110, a drawer 120, and a pull out distance limiting part 130, as shown in FIGS. 1 through 5. Hereinafter, each component will be described with reference to FIGS. 1 through 5.

The drawer housing 110, as shown in FIG. 1, is a component forming an exterior of the case 100 for the coin tissue of the present disclosure. The drawer housing 110 may include, as shown in FIGS. 1, 2, and 5, an insertion space 111 into which the drawer 120 is inserted, and a push-in and pull-out portion 112 communicated with the insertion space 111 and by which the drawer 120 is pulled in or pulled out.

Furthermore, the push-in and pull-out portion 112 of the drawer housing 110 may be an opening in a front surface of the drawer housing 110 as shown in FIGS. 1 and 5, and the size of the push-in and pull-out portion 112 may be determined such that a coin tissue 10 in the drawer 120 is smoothly pulled in and out by the push-in and pull-out portion 112 while the drawer 120 is pulled in or pulled out. For example, the push-in and pull-out portion 112 may be an opening having a height greater than a diameter of the coin shape tissue 10.

As shown in FIGS. 1 and 5, the drawer 120 is a component used for substantially placing a plurality of coin tissues 10. As shown in FIGS. 1, 2, and 5, the drawer 120 may be pushed into or pulled out of the insertion space 111 of the drawer housing 110 in a slidable manner through the push-in and pull-out portion 112 of the drawer housing 110. In addition, the drawer 120 may have an upper opening portion for accommodating the coin tissue 10 as shown in FIGS. 1, 2, and 4, in which the plurality of coin tissues 10 may be placed in one or more rows (see L21 or L22 shown in FIG. 2).

Furthermore, the drawer 120 may include a drawer body 121 and a tissue pull-out guide groove 122, as shown in FIGS. 1 through 3 and 5. The drawer body 121 may have the upper opening portion as mentioned above and provide a space for placing the coin tissue 10 received through the upper opening portion. The tissue pull-out guide groove 122, which is formed at a side surface of the drawer body 121 and relatively lower than a height of the side surface of the drawer body 121, may guide the coin tissue 10 to be pulled out.

Therefore, when a user pushes aside a coin tissue 10 at a first position of a row in a state where the drawer 120 is pulled out about a first distance (see an arrow mark shown in FIG. 2), the coin tissue 10 may easily pass the tissue pull-out guide groove 122, and the user may easily pull-out the coin tissue 10 from the drawer 120.

In addition, the drawer 120 may further include a cover 123, as shown in FIGS. 1 and 5. The cover 123 may be provided at a front surface of the drawer body 121 and tightly close the push-in and pull-out portion 112 of the drawer housing 110 when the drawer body 121 is pushed into the drawer housing 110.

In addition, when the one or more rows described above include a first row and a second row, the drawer 120 may include, as shown in FIGS. 1 and 2, a first row rest part L21, a second row rest part L22, and an intermediate partition L23. The first row rest part L21 may place some of the plurality of coin tissues 10 in an arrangement of the first row, and the second row rest part L22 may place others of the plurality of coin tissues 10 in an arrangement of the second row. The intermediate partition L23 may divide the first row rest part L21 and the second row rest part L22 such that the coin tissue 10 does not cross a row and is smoothly aligned. Therefore, a large number of coin tissues 10 may be preserved by setting the one or more rows, in which the plurality of coin tissues 10 are placed, as a plurality of rows.

The pull-out distance limiting part 130 is a component for limiting a pull-out distance of the drawer 120. The pull-out distance limiting part 130 may be provided between an inner surface of the drawer housing 110 and an outer surface of the drawer 120, as shown in FIG. 2, and limit the pull-out distance of the drawer 120 as a first distance. For example, the first distance may be determined approximately as a thickness of the coin tissue 10.

Accordingly, in a state where the plurality of coin tissues 10 are placed in the drawer 120 in one or more rows, the pull-out distance of the drawer 120 is limited as the first distance (for example, about the thickness of the coin tissue) by the pull-out distance limiting part 130 and the drawer 120 may be pulled out of the drawer housing 110. That is, only a first coin tissue of a row may be exposed to outside without exposing all of the plurality of coin tissues 10, and therefore, each of the coin tissues 10 kept in the case 100 for the coin tissue 10 may be maintained as sanitary as possible.

For example, the pull-out distance limiting part 130 may include a locking groove 131 and a locking protrusion 132 as shown in FIG. 2. The locking groove 131 may be formed in a long groove shape in the inner surface of the drawer housing 110, and the locking protrusion 132 may be provided at the outer surface of the drawer 120 to be locked at the locking groove 131. Although not shown, the locking groove 131 may be formed in the outer surface of the drawer 120 and the locking protrusion 132 may be provided in the inner surface of the drawer housing 110.

In addition, the case 100 for coin tissue according to an embodiment of the present disclosure may further include a wet tissue production part 140 as shown in FIGS. 1, 2, and 5. The wet tissue production part 140 may be provided in the outer surface of the drawer housing 110. Particularly, although not shown, the wet tissue production part 140 may have the form of a container to contain water and may accommodate the coin tissue 10 such that the coin tissue 10 pulled out of the drawer 120 is soaked by the water in the wet tissue production part 140.

Therefore, the user may pour water into the wet tissue production part 140 and directly take out the coin tissue 10 from the drawer 120 and put the coin tissue 10 into the wet tissue production part 140 that contains the water. The coin tissue 10 in a compressed state may swell up without an extra tool such as a container and be directly used as wet tissue.

Furthermore, the wet tissue production part 140 may be provided in a recessed manner in the outer surface of the drawer housing 110 as shown in FIGS. 1 and 5. Since the first row rest part L21, as shown in FIGS. 2 and 5, may be provided in a relatively short length not to interfere with the wet tissue production part 140 provided in a recessed manner, the wet tissue production part 140 may be provided as a recessed space. Although not shown, the wet tissue production part 140 may be provided by reducing the length of the second row rest part L22.

In addition, the case 100 for coin tissue according to an embodiment of the present invention may further include a tilt prevention part 150 as shown in FIGS. 1, 4, and 5. The tilt prevention part 150 may prevent the drawer 120 from tilting against the drawer housing 110 while the drawer 120 is being pulled out. Therefore, while the drawer 120 is being pulled out of the drawer housing 110, the drawer 120 maintains a length direction with respect to the drawer housing 110 without moving up and down against the drawer housing 110 and may be smoothly and stably pulled out.

For example, as shown in FIGS. 4 and 5, the tilt prevention part 150 may include a guide rail 151 and a rail contact surface 152. The guide rail 151, which protrudes from the inner wall of the drawer housing 110, may be provided long along the direction in which the drawer 120 is pulled in and out. The rail contact surface 152 may constitute an upper end of the side surface of the drawer body 121 and slidably contact with a bottom surface of the guide rail 151.

Furthermore, as shown in FIG. 5, a rest surface L20 in the drawer body 121, which is the surface on which the plurality of coin tissues 10 are placed, may include a smooth surface.

Therefore, when the case 100 for coin tissue of embodiments of the present invention is inclined such that the front of the case 100 faces downward, the plurality of coin tissues 10 can be easily moved together to the front of the case 100. Thus when the drawer 120 is open (that is, pulled out), the first coin tissue in a row is always ready to come out.

In addition, as shown in FIG. 4, the rest surface L20 of the drawer body 121, on which the coin tissue 10 is placed, may have an arc shaped cross-section. Accordingly, the coin tissue 10 may be prevented from falling down in the drawer body 121, and as the coin tissue 10 easily slips, it is easy to incline the drawer 120 and pull out the coin tissue 10.

As described above, the case for coin tissue according to embodiments of the present invention may have the following effects.

According to an embodiment of the present invention, since a case for coin tissue provides the technical configuration including the drawer housing, the drawer, and the pull-out distance limiting part. The plurality of coin tissues may be placed in the drawer in one or more rows, and the drawer may be pulled out of the drawer housing with a pull-out distance of the drawer limited to the first distance by the pull-out distance limiting part. That is, only a first coin tissue of the row may be exposed to outside without exposing all of the plurality of coin tissues to the outside, and therefore, each of the coin tissues kept in the case for the coin tissue may be maintained as sanitary as possible.

In addition, according to an embodiment of the present invention, the technical configuration in which the drawer includes the drawer body and the tissue pull-out guide groove is provided. Therefore, when a user pushes aside the first coin tissue of the row in the state where the drawer is pulled out about the first distance, the coin tissue may easily pass the tissue pull-out guide groove and the user may easily pull out the coin tissue from the drawer.

Furthermore, according to an embodiment of the present invention, the technical configuration further including the wet tissue production part at the outer surface of the drawer housing is provided. Therefore, the user may pour water into the wet tissue production part and directly take out the coin tissue from the drawer and put the coin tissue into the wet tissue production part that contains the water, and the coin tissue in the compressed state may swell up without using an extra tool such as a container and be directly used as wet tissue.

In addition, according to an embodiment of the present invention, a large number of coin tissues may be sanitarily preserved by setting the one or more rows, in which the plurality of coin tissues are placed, as a plurality of rows.

Furthermore, according to an embodiment of the present invention, the technical configuration further including the tilt prevention part between the drawer housing and the drawer is provided. Therefore, the drawer may be smoothly and stably pulled out and maintain the length direction without being inclined with respect to the drawer housing.

In addition, an embodiment of the present invention provides the technical configuration in which the rest surface in the drawer body, which is the surface on which the plurality of coin tissues are placed, includes a smooth surface. Therefore, when the case for coin tissue is inclined such that the front of the case faces downward, the plurality of coin tissues may be easily moved to the front of the case, and the coin tissue at the first position of the row may be always ready to come out when the drawer is open (that is, when the drawer is pulled out).

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in forms and details may be made therein without departing from the spirit and scope of the disclosure as defined by the following claims.

What is claimed is:

1. A case for coin tissue, the case comprising:
    a drawer housing comprising an insertion space;
    a drawer configured to be pushed into or pulled out of the insertion space in a slidable manner, the drawer comprising:
        a drawer body comprising a pair of opposing side walls and an upper opening portion, coin tissues being placed in one or more rows in the drawer body; and
        a tissue pull-out guide groove formed at each of the side walls of the drawer body, wherein the tissue pull-out guide groove has a height lower than a top of the side walls of the drawer body, and wherein the tissue pull-out guide groove is configured to guide a first coin tissue of the coin tissues located at a front of the drawer among the coin tissues placed in the drawer body to be pulled out;

a pull-out distance limiting part provided between an inner surface of the drawer housing and an outer surface of the drawer, and configured to limit a pull-out distance of the drawer to a first distance, wherein the first distance is determined as a distance corresponding to a thickness of the first coin tissue;

a wet tissue production part provided in a recessed manner in an outer surface of the drawer housing, wherein the wet tissue production part is configured to accommodate the first coin tissue pulled out of the drawer body so that the first coin tissue is soaked by water provided in the wet tissue production part; and a tilt prevention part configured to prevent the drawer from inclining against the drawer housing while the drawer is being pulled out, wherein the tilt prevention part comprises a guide rail attached to an inner wall of the drawer housing and extending along a direction in which the drawer is pushed in and pulled out, and wherein the drawer body slidably contacts a bottom surface of the guide rail.

* * * * *

UNITED STATES PATENT AND TRADEMARK OFFICE
CERTIFICATE OF CORRECTION

| | | |
|---|---|---|
| PATENT NO. | : 10,988,283 B2 | Page 1 of 1 |
| APPLICATION NO. | : 16/552977 | |
| DATED | : April 27, 2021 | |
| INVENTOR(S) | : Wan Gu Lee | |

It is certified that error appears in the above-identified patent and that said Letters Patent is hereby corrected as shown below:

In the Claims

In Column 6, Line 60, Claim 1, after "of" delete "opposing".

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*